United States Patent [19]

Hansen

[11] Patent Number: 4,900,684
[45] Date of Patent: Feb. 13, 1990

[54] CEA IMMUNOASSAY FREE OF HUMAN ANTI-MOUSE ANTIBODY FALSE POSITIVES

[75] Inventor: Hans J. Hansen, Flemington, N.J.

[73] Assignee: Immunomedics, Inc., Warren, N.J.

[21] Appl. No.: 56,571

[22] Filed: Jun. 1, 1987

[51] Int. Cl.$^4$ .................... G01N 33/543; G01N 33/53
[52] U.S. Cl. ................................. 436/518; 436/548; 436/825; 435/7
[58] Field of Search ...................... 436/518, 548, 825; 435/7

[56] References Cited

U.S. PATENT DOCUMENTS 4,272,504  6/1981  Kim et al. ........................... 436/531
4,299,815  11/1981  Hansen et al. ........................ 435/7

OTHER PUBLICATIONS

McLaughlin et al., *Clinica Chimica Acta:* 130, 199-209 (1983).
Kim et al., Clin. Chem., 25:773-776 (1979).
Hirai, Cancer Research, 37:2267-2274 (Jul. 1977).
Keep et al., VIIth Meeting, International Society for Oncodevelopmental Biology and Medicine, No. 176, p. 14.30 (1970).
Epenetos et al., Brit. J. Radiol., 59:117-125 (1986).

*Primary Examiner*—Robert J. Warden
*Assistant Examiner*—Janelle Graeter
*Attorney, Agent, or Firm*—Bernhard D. Saxe

[57] ABSTRACT

A CEA immunoassay includes a step for inactivation of interfering human antibodies against non-human immunoglobulin, wherein a buffered serum or plasma sample at about pH 5.0 is heated at about 90° C. for about 15 minutes prior to sandwich assay using capture and probe monoclonals that bind to heat-stable CEA epitopes.

26 Claims, No Drawings

CEA IMMUNOASSAY FREE OF HUMAN ANTI-MOUSE ANTIBODY FALSE POSITIVES

BACKGROUND OF THE INVENTION

The present invention relates to an improved immunoassay method for determining carcinoembryonic antigen (CEA) in a serum sample, which corrects for false positives due to the presence in the sample of human anti-species antibodies.

It is well known to carry out immunoassays for antigens which may be present in the serum or other body fluids of a patient, in order to obtain diagnostically useful information. These immunoassays may use one or more polyclonal or monoclonal antibodies. The presence of heterophile antibodies in human serum has long been recognized. Heterophile antibodies are antibodies that bind to several species of non-human immunoglobulins. Some immunoassays include one or more animal sera as components of the diluent to coagulate heterophile antibodies, since these antibodies can interfere with assay.

It is also known to heat acidified human serum or plasma samples to coagulate interfering matrix protein, or "inert proteins". Hirai, *Cancer Research*, 37:2267–2274, 1977, disclosed pretreatment of serum samples for a dual polyclonal antibody radioimmunoassay (RIA) for CEA. Dilute serum samples, buffered at pH 5, were heated at 85° C. for 10 minutes prior to immunoassay to avoid interference from inert proteins in serum. Kim et at., *Clin. Chem.*, 25:773–776, 1979, disclosed heat treatment of plasma and serum samples at pH 5, at a temperature of 70°–80° C., for 10–20 minutes, prior to dual polyclonal antibody RIA, to coagulate "non-specific proteins" in the sample that interfered with CEA determination.

In an abstract distributed to attendees at the VIIth Meeting of the International Society for Oncodevelopmental Biology and Medicine, entitled Tumor Markers, held in Surrey, England, in September, 1979, Keep et al., abstract No. 176, disclosed that heat treatment of CEA-containing extracts of human tumors and of normal colon and meconium led to a reduction in measured CEA values, using a dual polyclonal antibody RIA and a dual antibody polyclonal enzyme immunoassay (EIA). The effect was reportedly masked by human serum components, however, and these authors reported that heat treatment of patient' sera at 85° C. for 10 minutes did not diminish their CEA levels as measured by both RIA and EIA. The presence of "heat-labile and heat-stable components of CEA" was noted, and polyclonal antisera raised against heat-treated CEA were mentioned, as was a polyclonal antiserum that reacted predominantly with heat-labile CEA. These authors also noted that dilution of CEA with serum or immunoglobulin appeared to confer some protection to CEA with respect to heat treatment.

The recent trend to use of monoclonal antibodies, especially murine monoclonals from ascites production or raised in cell culture, in sandwich assays has led to a recognition that human anti-species antibodies in serum can sometimes interfere with such assays and lead to false positive results. For example, a sandwich assay for CEA in human serum or plasma, using a pair of murine monoclonal capture and probe antibodies, would show a false elevation in the presence of substantial amounts of human anti-mouse antibodies (HAMA), since such antibodies could bridge the capture and probe antibodies by binding of one arm of the anti-mouse antibody to each.

A need exists for a CEA immunoassay method which can include as an optional step a simple procedure for eliminating falsely elevated readings due to the presence of human anti-non-human species antibodies such as HAMA. Such an assay would be of particular value to clinicians who need to determine and monitor CEA levels in cancer patients, especially those who may have been treated or are being treated with murine monoclonal antibodies for tumor imaging or therapy. As other types of non-human monoclonal or polyclonal antibodies are developed for in vivo use, the method of the invention will serve a wider market.

OBJECTS OF THE INVENTION

The primary object of the present invention is to provide an immunoassay method for determining CEA in a human serum or plasma sample which may contain interfering human antibodies against non-human species antibodies, wherein such interfering antibodies are inactivated without inactivating the CEA in the sample, thereby avoiding a false positive elevation in the CEA titer. In particular, the assay should incorporate an optional step for inactivation of HAMA in patients who may have elevated HAMA levels as a result of treatment with murine monoclonal antibodies. More generally, the assay should be useful for determining other heat-stable antigens.

Upon further study of the specification and appended claims, further objects and advantages of this invention will become apparent to those skilled in the art.

SUMMARY OF THE INVENTION

These objects are achieved by providing an immunoassay for determining carcinoembryonic antigen (CEA) in a human serum or plasma sample which may also contain interfering human antibodies that bind non-human antibodies, comprising the steps of:

(a) heating a serum or plasma sample, buffered at a pH of about 4.5–5.5, at a temperature of about 80°–105° C., for about 10–30 minutes, separating insoluble material and recovering the resultant solution:

(b) incubating the recovered solution with a capture monoclonal anti-CEA antibody bound to a solid phase, and with a probe monoclonal anti-CEA antibody carrying a detectable label, each of said capture and probe antibodies being an antibody which binds to a different heat-stable epitope on CEA, the incubation being effected such that the CEA in the sample binds to the capture antibody, and the bound CEA binds labeled probe antibody, and separating unbound sample components and unbound labeled probe antibody from the solid phase; and (c) determining the amount of CEA in the sample as a function of the amount of labeled probe bound to the solid phase or the amount of unbound labeled probe separated from the solid phase.

DETAILED DISCUSSION

Murine monoclonal antibodies have recently been used for in vivo imaging and therapy in patients suffering from cancer, heart disease and various infectious diseases. In many of these treatment courses, it has been noted that human antibodies against mouse immunoglobulin are stimulated and may rise to rather high levels in the patient's bloodstream. The presence of HAMA can complicate the in vivo adminstration of murine monoclonal antibodies by eliciting certain toxic side effects or by interfering with the intended functional activity of the monoclonal.

Elevated HAMA titers have been observed in cancer patients who have received radiolabeled murine monoclonal anti-CEA antibodies for radioimmunotherapy. The CEA levels in the plasma of such patients are routinely monitored during the course of therapy, and apparent rising CEA titers were observed, along with rising HAMA titers. Absorption of these plasmas with solid-phase anti-human immunoglobulin-G (IgG) or with protein-A restored CEA titers to pretreatment levels, demonstrating that the serum factor eliciting false positive CEA titers was most likely due to HAMA. Neither the addition of neat mouse serum to the assay nor pretreatment of the sample by heating to 70° C. for 15 minutes, at pH 5.0, effectively abolished HAMA interference.

By contrast, protein precipitation with 13% polyethylene glycol (PEG) or heating the plasma samples to 90° C. for 15 minutes, at pH 5.0, eliminated false positive CEA titers caused by HAMA. Heat pretreatment of plasma at 90° C. did not reduce authentic CEA titers in patients without HAMA, nor did it change CEA levels in normal controls, showing that such heat treatment of serum or plasma samples, according to the present invention, can be included as an optional step in CEA immunoassays, which is an effective and simple means of eliminating HAMA interference in specimens intended for CEA quantitation.

Although it was known that CEA retained immunological activity after brief heat treatment at up to 95° C. at pH 5.0, it could not be predicted that an assay could be developed using a pair of monoclonal antibodies, each of which binds to a different heat-stable epitope on CEA, and that heat treatment of serum or plasma samples according to the method of the present invention would inactivate substantially all of the human anti-non-human species antibodies in the sample without impairing binding of the capture and probe monoclonals of the assay to the CEA in the treated sample.

In the heat treatment step of the assay, a human serum or plasma sample is buffered to a pH of 4.5–5.5, preferably 4.75–5.25, and more preferably above 5.0, i.e., 4.9–5.1, which is normally the range of accuracy of pH 5.0 acetate or citrate buffer. The latter buffers are preferred, although other buffers generally recognized as equivalent in the immunoassay art can also be used. The buffered sample is heated at a temperature of 80°–105° C., preferably 85°–100° C., more preferably 90°–95° C. and most preferably at about 90° C. The heating time at the selected temperature is 10–30 minutes, preferably 10–20 minutes and more preferably for about 15 minutes.

It will be appreciated that heating conditions of pH 5.0, 90° C. and 15 minutes represent optimum values, but that some variation is possible. It will also be appreciated that shorter heating times are consistent with higher temperatures, and that the pH of about 5.0 is generally considered optimal for coagulation of the interfering antibodies but may vary in certain samples if the patient's interfering immunoglobulins have unusual amino acid distributions and isoeletric points.

Murine monoclonal anti-CEA antibodies that bind to heat-stable epitopes on CEA are known. For example, the monoclonals designated NP-1 and NP-3 disclosed by Primus et al., in U.S. patent application No. 005,355, filed Jan. 12, 1987 and incorporated herein in its entirety by reference, which are examples of generic antibodies having the property that they bind to particular CEA epitopes, can be used as a pair in a CEA immunoassay according to the present invention, where NP-1 is the capture and NP-3 is the probe. The heat stability of the epitopes to which these antibodies bind has not been disclosed earlier.

It is known, as disclosed, e.g., by Keep et al., supra, that antibodies can be raised against heat-treated CEA, although these authors only prepared polyclonal antisera against heat-treated CEA. However, the present inventor has now shown that monoclonals suitable for use as capture and probe in a CEA assay according to the invention can also be prepared. The normal methods of screening monoclonals are used, with the further caveat that heat-treated CEA, i.e., CEA buffered at pH 5.0 and heated at 90° C. for about 15 minutes, is used to assay binding specificities and affinities for the clones, in order to assure that the anti-CEA antibodies bind to heat-stable CEA epitopes, defined operationally in terms of the ability of such epitopes to survive the foregoing heat treatment when the CEA is heated in serum or in a solution containing sufficient serum components to stabilize it against loss of immunoreactivity in a standard assay such as the Roche RIA or the Abbott EIA, in either polyclonal or monoclonal forms.

Plasma CEA titers of HAMA-negative patients were measure using the immunoassay according to the method of the present invention and using the same immunoassay otherwide identical but without heating at 90° C. for 15 minutes, and it was established that the heat treatment itself did not in itself cause changes in apparent CEA titers in the absence of HAMA.

Heating serum or plasma samples at 70° C. rather than at 90° C. was not effective in eliminating HAMA activity or suppressing apparent elevation in CEA titers. In patients with elevated HAMA titers, i.e., titers above 20,000, dilution of the sample with neat mouse serum was tried to neutralize the HAMA. The HAMA titer is defined herein as the reciprocal of the sample dilution required to obtain an O.D. (optical density) reading of 1 in the HAMA assay described below. A HAMA titer of 20,000 corresponds to a HAMA level of about 5,000 ug/ml in this assay. Only when an equal volume of neat mouse serum was added to the plasma specimen did a reduction in CEA titer appear, but the neutralization of HAMA was still incomplete since the CEA titer remained artificially elevated.

Although neutralization of specimens with lower HAMA titers was not studied, and it is possible that addition of significant amounts of neat mouse serum could neutralize all of the HAMA activity in the sample, this would still be a significantly more costly alternative to heat treatment and would use a diluent which could add other undesirable components to the assay if used in such quantity. Even the further presence of 1% mouse serum in some assays for CEA did not suffice to neutralize interfering level of HAMA when combined with heat treatment at 70° C.

The method of the present invention is a simple and effective option for use in determining the CEA titer of patients who may have elevated levels of interfering human antibodies against non-human antibodies used in immunoassays. It will be appreciated that the heat treatment can be omitted for the assay of patients known not to have interfering levels of Hama or HAMA-like antibodies, without changing the other steps in the assay procedure.

It will also be appreciated that the method of the present invention will also eliminate interfering antibodies against other non-human antibodies than mouse antibodies. This may be useful in the future if other types of non-human monoclonal antibodies become more accessible for commercial use in immunoassays. For example, mouse-primate fusions, or fusions of other non-human immortal proliferative cell lines with splenocytes from various animals could be used to produce hybrids which secrete monoclonal antibodies and could be propagated by ascites production, cell culture or other as yet undefined means. Thus, it is the epitopic specificity of the monoclonals, and not their method of production or species, so long as they are not human monoclonals, that will determine their utility in CEA immunoassays and their reactivity with human monoclonals which may arise if similar antibodies are used for in vivo diagnostic or therapeutic use in the patient.

It will also be appreciated that the method of the invention will be applicable to dual isotope immunoassays for other analytes which are stable to heat treatment for inactivation of HAMA-like antibodies, and which fit the other criteria for an immunoassay set forth for CEA in the foregoing discussion. It must be the case that an immunoassay for the analyte uses a suitable pair of capture and probe monoclonal antibodies that each bind to a heat-stable epitope on the analyte. Another example of such an assay is a dual antibody assay for alkaline phosphatase (AP), a marker which is associated with ovarian cancer. Dual antibody assays for AP are known, e.g., the assay described in Epenetos et al., *Brit. J. Radiol.*, 59:117–125, 1987. This assay uses capture and probe antibodies that bind to heat-stable epitopes on AP, and would be useful to monitor patients receiving monoclonal antibody reagents for tumor imaging or therapy. Other cancer-associated markers, e.g., lysozyme, prostatic acid phosphatase, tumor mucins and the like, also have been assayed with dual monoclonal antibody assays, and are heat-stable. Such assays can also include a heat treatment according to the present invention for use in patients with high levels of HAMA-like antibodies.

As the use of monoclonal antibodies from non-human species for in vivo medical application becomes more common, it will be of increasing importance to exercise caution in the interpretation of any in vitro immunoassay using monoclonal antibodies, when the sample is serum or plasma from a treated patient in which the presence of elevated titers of HAMA or HAMA-like antibodies is suspected. This may require measurement of the sensitivity of the assay to interference from HAMA-like antibodies and, where necessary, methods may need to be devised to eliminate the problem. Heat treatment according to the invention is a simple and effective expedient for CEA assays, but removal of HAMA-like antibodies with solid-phase anti-human IgG or protein-A or PEG precipitation may be required for other assays where either the analyte as a whole is not stable to the heat treatment or the epitopes to which appropriate monoclonals can be raised are not heat-stable.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

Enzyme Immunoassay for CEA

The concentration of CEA in an untreated or heat treated plasma sample was determined by a sandwich EIA using two monoclonal antibodies against CEA. A microtiter plate sensitized with monoclonal antibody 31C5A4 at 10 ug/ml in PBS was washed with PBS containing 0.05% Tween-20. Plasma samples (100 ul) or standards were added to wells containing 100 ul of buffer composed of PBS with 10% heat-inactivated horse serum and 1% mouse serum. Ortho Tri-level Ligand Assay Control Sera (Ortho Diagnostics, Raritan, N.J.) containing different concentrations of CEA served as the standards. After a 90 min. incubation at 37° C., the plates were washed and 200 ul of peroxidase-conjugated monoclonal antibody 20C2H1 diluted in PBS-Tween were added to the wells. After 30 min at 37° C., the plates were washed and 200 ul of substrate solution prepared from O-phenylenediamine dihydrochloride (OPD) tablets (Pittman-Moore, Amwell, N.J.) was allowed to develop in the dark for 30 min at room temperature. The reaction was terminated with 50 ul of 4N $H_2SO_4$ and the plates were read at 490 nm. The concentration in the samples was determined by reference to the Tri-Level Control Sera standards.

EXAMPLE 2

Enzyme Immunoassay for HAMA

The antibody response of patients to mouse IgG was measured by EIA. Mouse IgG (Pelfreez Biologicals, Rogers, Ar) at 10 ug/mi in PBS was absorbed overnight at 4° C. to the wells of microtiter plates (Dynatech Laboratories, Alexandria, Va.). Dilutions of plasmas were incubated in the wells at 37° C. for 1 hr, washed, and then reacted with peroxidaseconjugated goat or mouse anti-human IgG (Jackson ImmunoResearch, Avondale, Pa.). The wells then received a substrate solution 0.0125% $H_2O_2$ and 4.4 mM o-phenylenediamine dihydrochloride (Sigma Chemical, St. Louis, Mo.) in 0.1M phosphate citrate buffer, pH 5.0. This was allowed to develop for 15 min before 4N $H_2SO_4$ was added and the plates read at 490 nm. The reciprocal dilution of plasma that gave an OD reading equal to 1.0 in the assay was referred to as the HAMA titer. A HAMA titer of 20,000 corresponds to a plasma sample content of about 500 ug/ml of HAMA.

EXAMPLE 3

Rise in Apparent CEA titers in Patients Injected With Monoclonals

While monitoring plasma CEA concentrations of colon carcinoma patients undergoing Phase I radioimmunotherapy with murine monoclonal anti-CEA antibody, a rather dramatic increase in CEA titer was observed in some patients. The corresponding plasma CEA and HAMA titers were measured for two patients who received 4 injections of monoclonal antibody, spaced at weekly intervals. At about 10 days after the first therapy injection, a rise in presumptive CEA titers was detected that rapidly increased 30 to 900 fold over the next 20 days. This increase in antigen titer paralleled a very similar rise in HAMA levels in both patients. After cessation of radioantibody treatment, both the CEA and HAMA titers decreased in a similar fashion. The correspondence between CEA and HAMA level suggested that bridging by HAMA of the two monoclonal antibodies used in the CEA immunoassay was responsible for the spurious elevations in CEA titers, despite the presence of 1% mouse serum in the diluent used in the CEA assay.

EXAMPLE 4

HAMA-Induced False Positive CEA Titers

To show that HAMA was indeed causing the interference in the measurement of CEA, plasma samples from two patients were exposed to an immunoadsorbent containing either anti-human IgG or protein-A bound to a solid phase (SP) (Table 1). In both cases, this manipulation caused a marked decrease in CEA titer, approaching levels very similar to pre-therapy antigen titers. As shown for Case 1, the HAMA titer was also reduced to negligible levels, particularly following exposure to protein-A. Similar manipulation of plasma from a patient, Case 3, (Table 1), who was not HAMA-positive, over the anti-human IgG or protein-A immunoadsorbents did not result in substantial changes in CEA titer, demonstrating that the effects on CEA titers noted in the other two patients were due to specific depletion of HAMA.

TABLE 1

Influence of Immunoglobulin Depletion on Plasma CEA Levels

| Plasma Treatment | Case 1$^d$ | | Case 2$^e$ | | Case 3 | |
|---|---|---|---|---|---|---|
| | CEA$^a$ | HAMA | CEA | HAMA | CEA | HAMA |
| None | 96 | 4600 | 576 | 49,500 | 158 | <10 |
| SP-Goat Anti-Human IgG | 12 | 46 | 24 | ND$^c$ | 169 | ND |
| SP-Protein A | 4 | <10 | 42 | ND | 183 | ND |

$^a$CEA level is in ng/ml.
$^b$HAMA titer is the reciprocal dilution of plasma which gives an O.D. of 1.0 in EIA.
$^c$ND, not determined.
$^d$Pre-therapy CEA value was 0.7.
$^e$Pre-therapy CEA value was 47.

EXAMPLES 5

Criticality of Temperature in Heat Treatment

Heat extraction of plasma specimens was carried out as follows: 1.0 ml of 0.2M sodium acetate buffer, pH 5.0 was added to 0.5 ml plasma. The tubes were vortexed and then incubated for 15 min at 70° C. or 90° C. prior to centrifugation at 1200×g for 10 min. The supernatants were collected and stored frozen until tested in the appropriate assay. As depicted in Table 2, heat extraction at 90° C., but not at 70° C., was more effective in eliminating HAMA activity and/or suppressing apparent CEA titers. These treatments did not significantly alter the CEA titer of the HAMA negative patient shown in Table 2 (Case 3).

TABLE 2

| Plasma Treatment | Case 1 | | Case 2 | | Case 3 | |
|---|---|---|---|---|---|---|
| | CEA$^a$ | HAMA$^b$ | CEA | HAMA | CEA | HAMA |
| None | 96 | 4600 | 576 | 49,500 | 158 | <10 |
| Heat Extract 70° C. | 13 | 540 | 359 | ND$^c$ | 147 | ND |
| Heat Extract 90° C. | 4 | <10 | 24 | ND | 112 | ND |

$^a$CEA level is in ng/ml
$^b$HAMA titer is the reciprocal dilution of plasma which gives an OD of 1.0 in EIA.
$^c$ND, not determined.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can made various changes and modifications of the invention to adapt it to various usages and conditions.

What is claimed is:

1. An immunoassay for determining carcinoembryonic antigen (CEA) in a human serum or plasma sample which may also contain interfering human antibodies that bind non-human species antibodies, comprising the steps of:
    (a) heating a serum or plasma sample, buffered at a pH of about 4.5–5.5, at a temperature of about 90°–105° C., for about 10–30 minutes, separating insoluble material and recovering the resultant solution:
    (b) incubating the recovered solution with a capture monoclonal anti-CEA antibody bound to a solid phase, and with a probe monoclonal anti-CEA antibody carrying a detectable label, each of said capture and probe antibodies being an antibody which binds to a different heat-stable epitope on CEA, the incubation being effected such that the CEA in the sample binds to the capture antibody, and the bound CEA binds labeled probe antibody, and separating unbound sample components and unbound labeled probe antibody from the solid phase; and
    (c) determining the amount of CEA in the sample as a function of the amount of labeled probe bound to the solid phase or the amount of unbound labeled probe separated from the solid phase.

2. The method of claim 1, wherein step (b) is effected by: (i) first incubating said recovered solution with said capture antibody bound to said solid phase, for a time sufficient for substantially all of the CEA in the sample to bind to the capture antibody, and then separating unbound sample components; and (ii) incubating the solid phase, containing bound CEA, with said labeled probe antibody, for a time sufficient for substantially all of the bound CEA to bind labeled probe antibody, and then separating unbound labeled probe antibody.

3. The method of claim 1, wherein step (b) is effected by: (i) first incubating said recovered solution with said labeled probe antibody, for a time sufficient for substantially all of the CEA in the sample to bind labeled probe antibody; and (ii) incubating the resultant solution with said capture antibody bound to said solid phase, for a time sufficient for substantially all of the CEA-probe complex in the sample to bind to the capture antibody, and then separating unbound sample components and labeled probe antibody from the solid phase.

4. The method of claim 1, wherein in step (a), the pH is 4.75-5.25.

5. The method of claim 4, wherein the pH is 4.9-5.1.

6. The method of claim 1, wherein in step (a), the temperature is about 90°-100° C.

7. The method of claim 6, where the temperature is 90°-95° C.

8. The method of claim 1, where in step (a), heating is effected for 10-20 minutes.

9. The method of claim 8, wherein the heating is effected for 15-20 minutes.

10. The method of claim 2, wherein in step (a), the pH is 4.75-5.25.

11. The method of claim 10, wherein the pH is 4.9-5.1.

12. The method of claim 2, wherein in step (a), the temperature is about 90°-100° C.

13. The method of claim 12, where the temperature is 90°-95° C.

14. The method of claim 2, where in step (a), heating is effected for 10-20 minutes.

15. The method of claim 14, wherein the heating is effected for 15-20 minutes.

16. The method of claim 3, wherein in step (a), the pH is 4.75-5.25.

17. The method of claim 16, wherein the pH is 4.9-5.1.

18. The method of claim 3, wherein in step (a), the temperature is about 90°-100° C.

19. The method of claim 18, where the temperature is 90°-95° C.

20. The method of claim 3, where in step (a), heating is effected for 10-20 minutes.

21. The method of claim 20, wherein the heating is effected for 15-20 minutes.

22. The method of claim 1, where in in step (a), the pH is about 5.0, and heating is effected at about 90° C. for about 15 minutes.

23. The method of claim 2, where in in step (a), the pH is about 5.0, and heating is effected at about 90° C. for about 15 minutes.

24. The method of claim 3, where in in step (a), the pH is about 5.0, and heating is effected at about 90° C. for about 15 minutes.

25. A method of removing human anti-species antibodies from human serum or plasma sample containing a heat-stable antigen, which comprises heating a human serum or plasma sample containing a heat-stable antigen and human anti-species antibodies, buffered at a pH of about 4.5-5.5, at a temperature of about 90°-105° C., for about 10-30 minutes, separating insoluble material and recovering the resultant solution.

26. An immunoassay for determining a heat-stable antigen in a human serum or plasma sample which may also contain interfering human antibodies that bind non-human species antibodies, comprising the steps of:
  (a) heating a serum or plasma sample, buffered at a pH of about 4.5-5.5, at a temperature of about 90°-105° C., for about 10-30 minutes, separating insoluble material and recovering the resultant solution:
  (b) incubating the recovered solution with a capture monoclonal antibody bound to a solid phase, and with a probe monoclonal antibody carrying a detectable label, each of said capture and probe antibodies being an antibody which binds to a different heat-stable epitope on said heat-stable antigen, the incubation being effected such that the antigen in the sample binds to the capture antibody, and the bound antigen binds labeled probe antibody, and separating unbound sample components and unbound labeled probe antibody from the solid phase; and
  (c) determining the amount of said antigen in the sample as a function of the amount of labeled probe bound to the solid phase or the amount of unbound labeled probe separated from the solid phase.

* * * * *